(12) United States Patent  (10) Patent No.: US 8,810,787 B2
Van Dorpe et al.  (45) Date of Patent: Aug. 19, 2014

(54) SINGLE MOLECULE OPTICAL SPECTROSCOPY IN SOLID-STATE NANOPORES IN A TRANSMISSION-BASED APPROACH

(75) Inventors: Pol Van Dorpe, Spalbeek (BE); Iwijn De Vlaminck, Delft (NL); Liesbet Lagae, Leuven (BE); Gustaaf Borghs, Leuven (BE)

(73) Assignees: IMEC, Leuven (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 0 days.

(21) Appl. No.: 13/133,525

(22) PCT Filed: Dec. 9, 2009

(86) PCT No.: PCT/EP2009/066737
§ 371 (c)(1),
(2), (4) Date: Jun. 8, 2011

(87) PCT Pub. No.: WO2010/066794
PCT Pub. Date: Jun. 17, 2010

(65) Prior Publication Data
US 2011/0249259 A1  Oct. 13, 2011

Related U.S. Application Data

(60) Provisional application No. 61/121,118, filed on Dec. 9, 2008.

(30) Foreign Application Priority Data

Dec. 9, 2008 (EP) .................................... 08171127

(51) Int. Cl.
*G01J 3/44* (2006.01)

(52) U.S. Cl.
USPC ............................................................ 356/301

(58) Field of Classification Search
CPC .................... G01N 21/658; G01N 33/48721
USPC .......................................................... 356/301
See application file for complete search history.

(56) References Cited

U.S. PATENT DOCUMENTS 3,708,673 A * 1/1973 Blacker, Jr. ............. 250/214 VT
7,177,236 B2 * 2/2007 Harchanko et al. ........ 369/13.33
(Continued)

FOREIGN PATENT DOCUMENTS

WO  WO03/016781  2/2003
WO  WO03/019245  3/2003

OTHER PUBLICATIONS

Downes, Andrew; Salter, Donald; Elfick, Alistair, "Simulations of atomic resolution tip-enhanced optical microscopy" Optics Express, vol. 14, No. 23, 2006.*

(Continued)

*Primary Examiner* — Gregory J Toatley
*Assistant Examiner* — Shawn Decenzo
(74) *Attorney, Agent, or Firm* — McDonnell Boehnen Hulbert & Berghoff LLP

(57) ABSTRACT

Methods and apparatus in the field of single molecule sensing are described, e.g. for molecular analysis of analytes such as molecular analytes, e.g. nucleic acids, proteins, polypeptides, peptides, lipids and polysaccharides. Molecular spectroscopy on a molecule translocating through a solid-state nanopore is described. Optical spectroscopic signals are enhanced by plasmonic field-confinement and antenna effects and probed in transmission by plasmon-enabled transmission of light through an optical channel that overlaps with the physical channel.

23 Claims, 4 Drawing Sheets

(56) References Cited

U.S. PATENT DOCUMENTS

| | | | | |
|---|---|---|---|---|
| 7,318,907 | B2* | 1/2008 | Stark et al. | 422/50 |
| 8,223,330 | B2* | 7/2012 | Natelson et al. | 356/301 |
| 2003/0015651 | A1 | 1/2003 | Kiguchi et al. | |
| 2005/0023156 | A1* | 2/2005 | Ramsey et al. | 205/792 |
| 2005/0110990 | A1* | 5/2005 | Koo et al. | 356/301 |
| 2008/0231834 | A1 | 9/2008 | Gryczynski et al. | |
| 2011/0036994 | A1* | 2/2011 | Frayling | 250/459.1 |
| 2012/0187305 | A1* | 7/2012 | Elam et al. | 250/390.01 |

OTHER PUBLICATIONS

PCT International Search Report and Written Opinion; PCT International Application No. PCT/EP2009/066737 dated May 7, 2010.

Keyser, Ulrich F. et al., "Nanopore Tomography of a Laser Focus", Nano Letters, vol. 5, No. 11, 2005, pp. 2253-2256.

European Search Report, European Application No. EP08171127 dated May 14, 2009.

Sischka, Andy et al., "Single Beam Optical Tweezers Setup with Backscattered Light Detection for Three-Dimensional Measurements on DNA and Nanopores", Review of Scientific Instruments, vol. 79, 2008, pp. 063702-1-063702-7.

Deamer, David W. et al., "Nanopores and Nucleic Acids: Prospects for Ultrarapid Sequencing", Trends in Biotechnology, vol. 18, No. 4, Apr. 1, 2000, pp. 147-151.

Keyser, Ulrich F. et al., "Direct Force Measurements on DNA in a Solid-State Nanopore", Nature Physics, vol. 2, No. 7, Jul. 2006, pp. 473-477.

Lezec, H.J. et al., "Beaming Light from a Subwavelength Aperture", Science, vol. 297, Aug. 2, 2002, pp. 820-822.

Muhlschlegel, P. et al., "Resonant Optical Antennas", Science, vol. 308, Jun. 10, 2005, pp. 1607-1609.

Perney, N.M.B. et al., "Tuning Localized Plasmon Cavities for Optimized Surface-Enhanced Raman Scattering", Physical Review, vol. 76, 2007, pp. 035426-1-035426-5.

Perney, Nicolas M. B. et al., "Tuning Localized Plasmos in Nanostructured Substrates for Surface-Enhanced Raman Scattering", Optics Express, vol. 14, No. 2, Jan. 2006, pp. 847-857.

Prodan, E. et al., "A Hybridization Model for the Plasmon Response of Complex Nanostructures", Science, vol. 302, Oct. 17, 2003, pp. 419-422.

Schuck, P.J. et al., "Improving the Mismatch Between Light and Nanoscale Objects with Gold Bowtie Nanoantennas", Physical Review Letters, vol. 94, 2005, pp. 017402-1-017402-4.

Smeets, R.M.M. et al., "Noise in Solid-State Nanopores", PNAS, vol. 105, No. 2, Jan. 15, 2008, pp. 417-421.

Garcia, F. J. et al., "Colloquium: Light Scattering by Particle and Hole Arrays", Reviews of Modern Physics, vol. 79, Oct.-Dec. 2007, pp. 1267-1290.

Genet, C. et al., "Light in Tiny Holes", Nature, vol. 445, Jan. 4, 2007, pp. 39-46.

Grupp, Daniel E. et al., "Beyond the Bethe Limit: Tunable Enhanced Light Transmission Through a Single Sub-Wavelength Aperture", Advanced Materials, vol. 11, No. 10, 1999, pp. 860-862.

Kim, W. et al., "Fractals in Microcavities: Giant Coupled, Multiplicative Enhancement of Optical Responses", Physical Review Letters, vol. 82, No. 24, Jun. 14, 1999, pp. 4811-4814.

Dekker, Cees, "Solid-State Nanopores", Nature Nanotech, vol. 2, 2007, pp. 209-215.

\* cited by examiner (a) (b)

SINGLE MOLECULE OPTICAL SPECTROSCOPY IN SOLID-STATE NANOPORES IN A TRANSMISSION-BASED APPROACH

CROSS-REFERENCE TO RELATED APPLICATIONS

The present application is a national stage application of International Patent Application no. PCT/EP2009/66737, which claims priority to U.S. Provisional Patent Application Ser. No. 61/121,118 and European Patent Application no. 08171127.7.

FIELD OF THE INVENTION

The present invention relates to methods and apparatus in the field of single molecule sensing. The methods and apparatus concern the molecular analysis of analytes such as molecular analytes, e.g. nucleic acids, proteins, polypeptides, peptides, lipids and polysaccharides.

TECHNICAL BACKGROUND

It is of importance to be able to sequence certain molecules, e.g. sequences of nucleic acids, proteins (poly-) and other complex biomolecular entities, for example in order to be able to do diagnostic screening.

In literature it is proposed that solid-state nanopores can be used for biochemical analysis {Dekker2007}, mostly structural analysis of linear organic molecules. A particular application that is often quoted is DNA sequencing {Deamer2000}. Solid-state nanopores are holes fabricated artificially in a membrane with diameter in the range (0.1 nm-999 nm). Molecular sequencing in such nanopore relies on translocation of the target molecule through the nanopore and subsequent transduction via highly localized physical interactions with the section of the molecule in the pore leading to measurable signals.

Transduction and recognition are performed sequentially and in real-time on segments of the molecule. Translocation is achieved passively or (with greater control) actively. Active translocation can be achieved by means of electrophoresis in which a voltage is applied on (two) electrodes placed in fluidic reservoirs separated by the membrane, the resulting electrical field then propels the charged molecule through the pore. In other examples optical or magnetic forces are exerted on the molecule or on bead(s) attached to the molecule to stimulate translocation or to modulate the translocation speed.

Various electric or electronic interactions can be exploited for sensing in the pore. For chemical analysis, chemically specific interactions are investigated. DNA translocation events are routinely detected by measurement of the ion current through the nanopore. The presence of a DNA molecule in the pore leads to an increase or decrease of the ionic current. Provided such measurements can be performed with sufficient sensitivity, information on structural or chemical composition of the molecule could be harvested from ionic current data. In another method, electrodes are mounted in the pore and electronic properties of the molecule are measured there. When a voltage is applied across the electrodes, an electronic current can flow stimulated by quantum mechanical electron tunneling via the electronic states of the molecule. Such mechanism provides chemical specificity. In yet another approach, capacitive modulations are sensed. {Dekker2007} specifically discloses a method called force spectroscopy on DNA in nanopores. Here, one end of the DNA is attached to a bead, which is trapped in the focus of an infrared laser. Subsequently, individual DNA molecules are inserted into a single nanopore and the DNA is arrested during voltage-driven translocation. The force acting on the DNA then pulls the bead away from the centre of the optical trap. This can be measured with high accuracy using the reflected light from the bead.

However all these methods are in need of improvement in order to obtain a more reliable result. Particularly, the force spectroscopy requires coupling between one end of a DNA molecule and a bead. Such coupling is an additional step that is undesired when intending to apply the method on a large scale for diagnostic use. Moreover, Dekker effectively senses that a bead is pulled away from the centre. There may be different causes, including side effects, impact of contaminants (e.g. other molecules present), viscosity and mass and heat transfer effects. Such different causes likely tend to reduce robustness and/or signal to noise ratio of the measurement.

WO03/16781 discloses a method of analyzing molecules such as DNA, wherein light is directed to a metal surface of a membrane having one or more apertures. Sidewalls of the apertures may be covered with metal, or alternatively, a thin, annular metallic ring may be present on the opposing surface of the substrate. The incident light excites surface plasmons (electron density fluctuations) in the top metal surface and this energy couples through the apertures to the opposing surface where it is emitted as light from the apertures or from the rims of the apertures. The extent to which surface plasmons are induced on the surface at the aperture exit may be limited, thereby constraining the resulting emissions to small target areas. The resulting spot illumination may be used to analyze the properties of small objects such as proteins and nucleic acid molecules and single cells.

The WO03/16781 discloses in its figure description more precisely how such analysis may be carried out. In one embodiment disclosed on page 39 and beyond, the document specifies that surface plasmon enhanced illumination can be used for implementation of an array based technique to study macromolecules and their interactions in solution, and to investigate cell surface phenomena in intact cells. The array can study different unlabeled macromolecules in parallel. The technique identifies the molecule using signatures that are isolated within a rich data set that is based on the macromolecules' interactions that yield measurable photonics effects or signatures. Detecting signatures is based on detecting changes in the emission spectra from the apertures indicating the presence and identity of the molecules affecting the changes. Light intensity may be detected with a CCD-detector. Alternatively, the device may be illuminated with monochromatic light that is scanned across the UV-visible-IR portion of the electromagnetic spectrum and the intensity monitored as the wavelength is scanned. Alternatively, shifts in resonance frequency may be detected.

It is observed that data shown in FIG. 29-32 of WO03/016781 do not reflect actual data. They are merely illustrative of the manner in which molecular characteristics may be manifested by intensity data, as acknowledged on page 42.

Furthermore, the WO03/016781 mentions the option of having ligands bound to the illumination side of the apertures and thereafter measure changes in intensity or wavelength. Here, it appears that the intended measurement is particularly a measurement of the number of devices. As acknowledged on page 50, first paragraph, the arrangement will display behaviour similar to a Geiger counter showing a count and a rate.

It is a disadvantage of WO03/016781 that it is after all not clear, how to obtain signatures that could be linked to the molecular structure. Moreover, the idea that identification of signatures could be based on comparison of a measured signal with a rich data set appears quite theoretical. The amount of macromolecular interactions yielding measurable photonics effects appears to be huge, and further appears in need for correction due to environmental effects. The analogy with the Geiger teller additionally suggests that the method of WO03/016781 is more suitable for counting molecules rather than for identification of the structure of the individual molecules.

SUMMARY OF THE INVENTION

An object of the present invention is to provide methods and apparatus in the field of single molecule sensing, e.g. for analysis of the molecular structure of analytes such as molecular analytes, e.g. nucleic acids, proteins, polypeptides, peptides, lipids and polysaccharides.

In one aspect the present invention provides an apparatus comprising:
a membrane having a first and a second major surface and having a membrane penetrating nanostructure between the first and second major surfaces,
a source of electromagnetic radiation that impinges radiation on the nanostructure in the direction of the first major surface,
means for translocating molecules through the nanostructure,
a detection unit for detecting electromagnetic radiation that exits from the nanostructure away from the second major surface, transmission of electromagnetic radiation through the nanostructure being at least by excitation of surface plasmon polaritons in the nanostructure,
wherein the penetrating nanostructure is further equipped with a field confining structure that create an electromagnetic hotspot.

In this invention use is made of an optical interaction. Plasmonic field-confinement and plasmon-enabled transmission of light through nanopores are used. Particularly, the invention makes use, in one embodiment, of a gap mode coupled to a surface plasmon cavity that displays similar functionality as a dipole antenna: the mode at a shape singularity such as a gap can be amplified in case an antenna structure (matched to the gap resonance) is constructed in its vicinity. These examples indicate that antenna structures or electromagnetic cavity structures can lead to stronger light collection and more pronounced resonance phenomena.

The present invention concerns molecular spectroscopy on a molecule translocating through a solid-state nanopore. Optical spectroscopic signals are enhanced by plasmonic field-confinement and, preferably, antenna effects and probed in transmission by plasmon-enabled transmission of light through an optical channel that overlaps with the physical channel.

The figures of merit for this optical method in the context of molecular analysis are spatial resolution and signal strength or signal-to-noise ratio. The plasmonic field-confinement is important in both enhancing the signals-to-be-detected and providing localization and thus spatial resolution. The plasmonic field confinement achievable is stronger than what can be achieved with traditional lens structures or photonic components. A smaller sensing region (hotspot) can thus be obtained.

The transmission-based approach provided by the present invention offers further background reduction and enhanced spatial resolution. The nanopore, that physically connects the upper and lower reservoir and that restricts molecular translocation and ionic current flow to a small section in the membrane, also functions as a light transmission channel in embodiments of the present invention. Hereby light transmission through the membrane via parasitic pathways, i.e. transmission through the membrane outside the pore region, is avoided. Hence, optical signals that do not interact with the optical device mounted on or in the membrane are restricted from reaching the detector, thereby eliminating unwanted background signals. A strong interaction between the light in the transmission channel and the molecule in the nanopore are thereby achieved.

This embodiment also leads to greater spatial resolution: optical signals arising from molecular excitations outside the sensing region have a reduced probability to be transmitted and to be collected by the optical detector. As a result, the embodiment provides an extra technique for achieving larger spatial resolution.

The field confining structure (e.g. nanoparticle(s) or a restricting channel constriction) creating an electromagnetic hotspot provides a smaller sensing region than what can be achieved with traditional lens structures or photonic components. The field confining structure provides plasmonic field confinement leading to localization based on gap mode resonance, at the hotspot.

It is observed that though WO03/016781 mentions means for confining the electronic excitation induced in that portion of the planar surface near the end of the aperture from which the light exits. This essentially states that the excitation is confined in a portion of one surface (i.e. at the exit side). The invention however confines the field within the nanostructure, which leads, as mentioned above, to gap mode resonance and amplification of the signal. As such, the invention creates an electromagnetic hotspot. The localization of the field again results therein that not merely the presence of molecules can be detected, but that also the structure of molecules or segments thereof can be identified Specific implementations for the field confinement includes antenna structures on the entry side and/or on the exit side, as well as nanopores having a varying diameter so as to restrict the field to a restricted volume.

Antenna structures can be added on the radiation entry side of the membrane to increase the portion of incident radiation that is collected and to achieve stronger field intensity in the penetrating nanostructure. On the radiation exit side an antenna can be used to increase the portion of radiation that is converted into free-space propagating radiation and/or to shape the exit beam.

Plasmonic nano-antennas can influence the behavior of optically active molecules in several ways. Firstly, due to the focusing of electromagnetic radiation to nanovolumes, molecules can be excited more efficiently. Secondly, the plasmon resonance perturbs the local electromagnetic mode density, modifying the decay rate of local dipole emitters. Such nano-antennas are particularly suitable in case that Raman spectroscopy, molecular fluorescence or surface enhanced infrared absorption spectroscopy is used.

In the case, e.g., of Raman spectroscopy, this double effect leads to the well known E4 dependence of the Raman scattering intensity on the local electric field. It further enables probing of vibrational transitions using optical excitation. Additional enhancement can be achieved using resonance Raman (illuminating in resonance with an electronic transition of the target molecule) or coherent anti-stokes Raman scattering (CARS) (a non-linear, 4-wave mixing process). Raman spectroscopy is particularly suitable for sensing segments of larger molecules, such DNA molecules.

In the embodiment of molecular fluorescence, there is a fundamental trade-off between field amplification by field confinement into the nanostructure and radiation that can leave the nanostructure, which is absent in the case of Raman. The shape of the pore is particularly relevant for the resolution, in order to limit the number of molecules contributing to the fluorescence. Nanoantennas located at the exit side lead again to a more effective outcoupling of radiation resulting from the fluorescence.

III Surface Enhanced Infrared Absorption spectroscopy. In this embodiment, infrared radiation is directly coupled into the nanostructure. Thereto, the antenna is provided with structures having a mutual pitch which is larger than the pitch in case of fluorescence or Raman. This radiation is again converted by excitation into radiation transmitted through the nanostructure.

The apparatus may include a first and second chamber and the membrane placed between the chambers. When analysing biomolecules, the first and second chamber are suitably filled with a liquid, for instance an aqueous medium, and then constitute a first and a second reservoir.

The means for translocating can include electrodes that may be placed in the first and second chambers and connected to a source of electrical power. Typically, a voltage difference is applied between such electrodes, such that molecules will be driven from the first to the second chamber. By virtue of the small size of the nanopore, with an appropriate voltage difference, the molecules may be translocated one by one. This allows measurement of individual molecules. More specifically, in one embodiment, the invention allows to measure groups within a larger molecule, for instance proteins within a DNA string. A resulting optical signal is then representative for the protein, such that order of proteins within a DNA-string is obtainable.

In one further embodiment, the voltage difference between the said electrodes is varied. More particularly, the voltage difference may be reversed. Therewith, movement of the molecule in the nanopore in the opposite direction may be achieved. Such reversed movement allows to repeat a measurement of at least a portion of the molecule. The repetition may be desired for obtaining a more robust measurement, for carrying out additional sensing. It may be further applied for carrying out a measurement in a scanning mode and in a high-resolution mode. In the scanning, the voltage difference will be larger (in absolute sense, independent of its orientation) than in the high-resolution mode. As a result, the molecule under investigation will be flower faster in the scanning mode than in the high-resolution mode. The scanning mode may for instance be used for obtaining a signal that can be compared with a reference signal. The high-resolution mode may be used for investigation at least a segment of the molecule that appear surprising, deviating or the like.

An optical detector may be placed in the second chamber or may be located next to the second chamber.

The nanostructure may be, for example, a pore or hole, e.g. circular, triangular, quadratic, oval or a slit or a channel.

The size of the nanopore is preferably very small: its diameter is suitably smaller than 100 nm and preferably smaller than 10 nm. The inner diameter of the nanopore may vary considerably depending on the intended use of the device. Typically, the channel or nanopore will have an inner diameter of at least about 0.5 nm, usually at least about 1 nm and more usually at least about 1.5 nm, where the—overall—diameter may be as great as 50 nm or longer.

In one implementation, such a nanopore with an inner diameter considerably smaller than the outer diameter comprises a pore with at least one side wall including an oblique (e.g. non-perpendicular) angle with the first major surface of the membrane. Preferably, the oblique angle is within the range of 25 to 75 degrees. It is observed for clarity that the nanopore in this implementation has a diameter that varies along its length, in a direction at least substantially perpendicular to the first surface of the membrane. The inner diameter is the smallest diameter along the length. The outer diameter is the largest diameter, typically such as present at an aperture of the nanopore located in least one of the surfaces of the membrane. The inner diameter may be located at a bottom of the nanopore, e.g. at or near to an aperture of the nanopore in the second surface of the membrane. The inner diameter may also be located at a position between the apertures corresponding to the first and the second surface. A restricted volume at the inner diameter may constitute an electromagnetic hotspot.

The membrane is optionally coated with metal on both sides or only on the entry or exit side, e.g. the first and the second surfaces of the membrane are coated with a metal. The metal may be patterned to define specific field confinement structures such as a nano-antenna.

Further, by optimizing the design of the pore/cavity system, the transmission can be maximized. Such design optimization comprises for instance nanostructuring of the metal on the first surface of the membrane to maximize the capture process and/or nanostructuring of the metal on the second surface (the backside) to maximize the re-emission process, Another aspect of the present invention provides a method for use with a membrane having a first and a second major surface and having a membrane penetrating nanostructure between the first and second major surfaces, the method comprising the steps of:

directing electromagnetic radiation onto the nanostructure in the direction of the first major surface, translocating molecules through the nanostructure, detecting electromagnetic radiation that exits from the nanostructure away from the second major surface, transmission of electromagnetic radiation through the nanostructure being at least by excitation of surface plasmon polaritons in the nanostructure.

Transition of e.m. radiation through the penetrating nanostructure is preferably a combination of up to three effects: surface plasmons, transmission of light and re-emission. "Surface plasmons" relates to free space e.m. radiation (the impinging radiation) being converted to surface plasmon polaritons in the coupled pore/cavity system. The dipolar excitation in the pore decays radiatively, resulting in enhanced transmission.

The membrane penetrating nanostructure is illuminated by e.m. radiation having a wavelength. The membrane penetrating nanostructure preferably has a size that is sub-wavelength.

In a specific embodiment, the translocating of molecules comprises translocating a molecule or a segment thereof in a direction from the first to the second surface and translocating the same molecule subsequently in an opposite direction, e.g. from the second surface towards to the first surface. Such reversed translocation and/or a repeated translocation towards the second surface allows to measure the segment again, or more profoundly. In one implementation the method thereto comprises a scanning mode and a high-resolution mode, in which scanning mode translocating the molecules occurs at a higher rate than in the high-resolution mode. The high-resolution mode then allows for optimum sensing.

According to a further aspect, the invention relates to a membrane having a first and a second major surface and having a membrane penetrating nanostructure between the first and second major surfaces, which membrane penetrating nanostructure comprises an electromagnetic hotspot. Preferably, the electromagnetic hot spot is created by means of at least one field confinement structure. Such field confinement structure is preferably a design of the membrane penetrating nanostructure with an inner diameter at the hot spot and an outer diameter at an aperture in at least one of the major surfaces, wherein the inner diameter is smaller than the outer diameter. Preferably, a side wall of the nanostructure is such that it includes an oblique angle with at least one of the major surfaces. A surface plasmon directing structure, such as an antenna, is suitably present on the first major surface.

According to an even further aspect of the invention, an apparatus for and a method of molecular spectroscopy are provided by means of translocating a molecule through a solid-state nanopore. Optical spectroscopic signals are enhanced by plasmonic field-confinement and, preferably, by antenna effects. Optical spectroscopic signals are probed in transmission by plasmon-enabled transmission of light through an optical channel that overlaps with the physical channel.

DEFINITIONS

Figure 1:
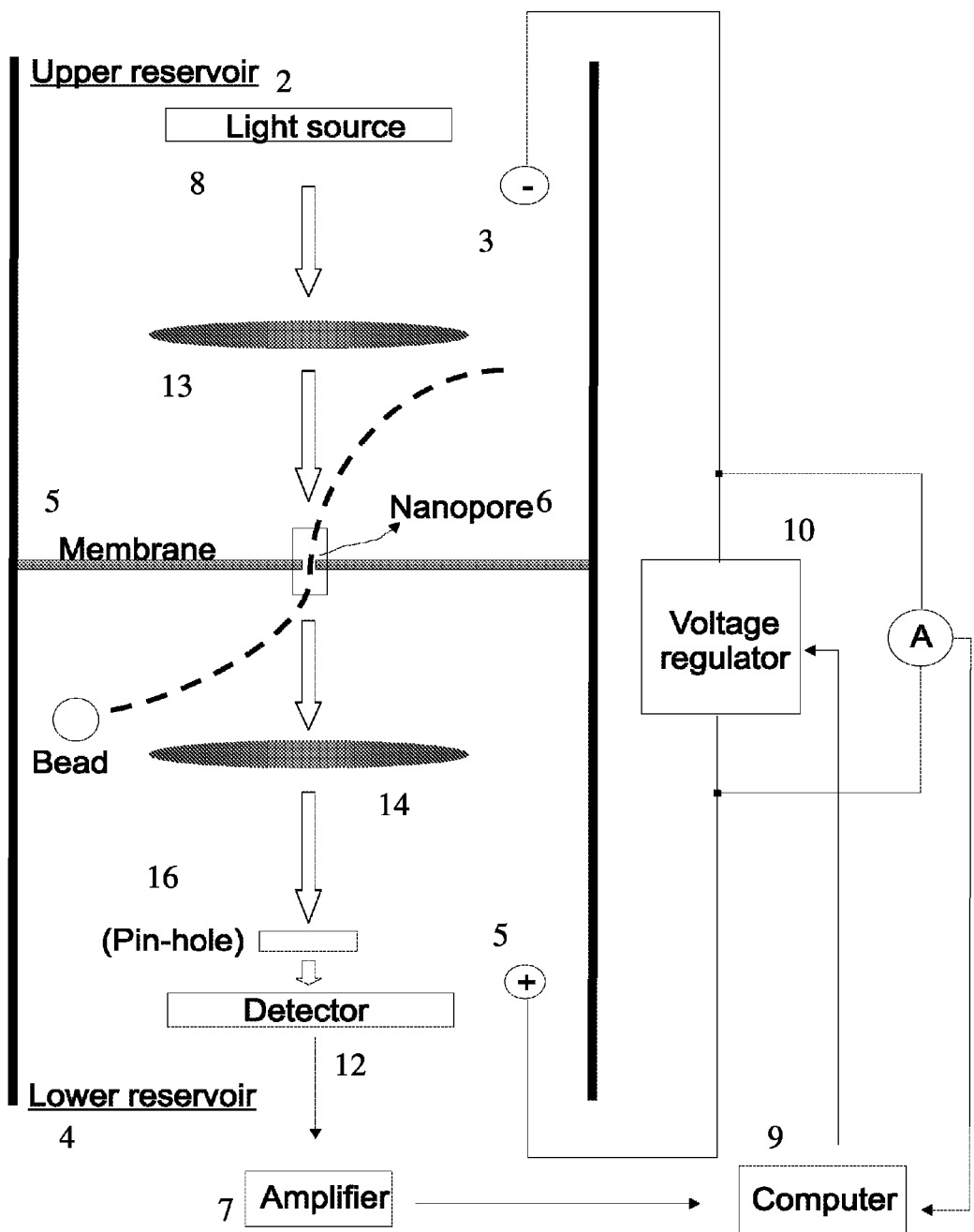
FIG. 1: schematic of the intended apparatus.

The term "membrane penetrating nanostructure" refers to a space through a membrane through which a molecule to be analyzed can pass. A membrane penetrating nanostructure should be understood as a structure having a nanoscale passageway through which a molecule can flow. The nanostructure is preferably designed such that the degrees of freedom for the movement of the molecule in the nanostructure is limited to a predefined direction, preferably from one side of the membrane to he other side of the membrane. Preferably, the movement should be limited to a 1D movement or line movement. The pore is not limited to the region through which the molecule flows, but can be larger such that light can be coupled in the nanostructure. Therefore, the membrane penetrating nanostructure can be a nanopore, a nanoslit or a nanochannel.

The nanostructure may be, for example, a pore or hole, e.g. circular, triangular, quadratic, oval or a slit or a channel. The pore can be round, spherical, rectangular or can have any shape and can have a varying diameter across the thickness of the membrane The term nanopore should be construed broadly to include nanoslits (two-dimensional equivalent) or nanochannels. A dimension which determines whether a molecule will pass, e.g. the distance across a slit, or the diameter of a hole, should be smaller than 100 nm and preferably smaller than 10 nm, e.g. less than 5 nm, less than 2 nm e.g. 1 nm. The membrane penetrating nanostructure will be illuminated by light having a wavelength. The membrane penetrating nanostructure has a size that is sub-wavelength.

The term "Nucleic acid" encompasses DNA, RNA, single-stranded, double-stranded or triple stranded and any chemical modifications thereof. Virtually any modification of the nucleic acid is contemplated. A "nucleic acid" may be of almost any length, from a small fragment up to a full-length chromosomal DNA molecule.

A "nucleoside" is a molecule comprising a purine or pyrimidine base or any chemical modification or structural analog thereof, covalently attached to a pentose sugar such as deoxyribose or ribose or derivatives or analogs of pentose sugars.

A "nucleotide" refers to a nucleoside further comprising at least one phosphate group covalently attached to the pentose sugar. The nucleotides to be detected may be ribonucleoside monophosphates or deoxyribonucleoside monophosphates although nucleoside diphosphates or triphosphates might be used. Alternatively, nucleosides may be released from the nucleic acid and detected. In other alternatives, purines or pyrimidines may be released, for example by acid treatment, and detected by Raman spectroscopy. Various substitutions or modifications may be made in the structure of the nucleotides, so long as they are still capable of being released from the nucleic acid, for example by exonuclease activity. For example, the ribose or deoxyribose moiety may be substituted with another pentose sugar or a pentose sugar analog. The phosphate groups may be substituted by various analogs. The purine or pyrimidine bases may be substituted or covalently modified. In embodiments involving labeled nucleotides, the label may be attached to any portion of the nucleotide so long as it does not interfere with exonuclease treatment.

A "Raman label" may be any organic or inorganic molecule, atom, complex or structure capable of producing a detectable Raman signal, including but not limited to synthetic molecules, dyes, naturally occurring pigments such asphycoerythrin, organic nanostructures, metal nanostructures such as gold or silver nanoparticles or nanoprisms and nano-scale semiconductors such as quantum dots. "Raman label" encompasses any organic or inorganic atom, molecule, compound or structure known in the art that can be detected by Raman spectroscopy. Fluorescence labels, SERS labels, quantum dots and other label-types can be chosen, e.g. other labels can be metallic particles or magnetic particles.

Certain embodiments of the invention can involve the use of nanoparticles to enhance the Raman signal obtained from nucleotides. The nanoparticles may be silver or gold nanoparticles, although any nanoparticles capable of providing a surface enhanced Raman spectroscopy (SERS), surface enhanced resonance Raman spectroscopy (SERRS) and/or coherent anti-Stokes Raman spectroscopy (CARS) signal may be used, e.g. Ag, Au, Cu, Al, Ni, Pt, Pd, particularly noble metals. A useful reference for particles and labels is: K. Kneipp, M. Moskovits, H. Kneipp (Eds.): Surface-Enhanced Raman Scattering—Physics and Applications, Topics Appl. Phys. 103, 1-18 (2006). Nanoparticles of between 1 nm and 2 nm in diameter may be used. Nanoparticles with an average diameter of 10 to 50 nm, 50 to 100 nm or about 100 nm are contemplated for certain applications. The nanoparticles may be approximately spherical in shape, although nanoparticles of any shape or of irregular shape may be used.

In certain embodiments of the invention, the nanoparticles may be random aggregates of nanoparticles (colloidal nanoparticles). In other embodiments, nanoparticles may be cross-linked to produce particular aggregates of nanoparticles, such as dimers, trimers, tetramer or other aggregates. Formation of "hot spots" for SERS, SERRS and/or CARS detection may be associated with particular aggregates of nanoparticles. Certain alternative embodiments may use heterogeneous mixtures of aggregates of different size or homogenous populations of nanoparticle aggregates. Aggregates containing a selected number of nanoparticles (dimers, trimers, etc.) may be enriched or purified by known techniques, such as ultracentrifugation in sucrose solutions.

DESCRIPTION OF EMBODIMENTS OF THE INVENTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Optical interactions greatly benefit from field confinement in the sensing region. Plasmon carrying metal structures are renowned for their ability to greatly increase field-confinement. Surface plasmons are electromagnetic excitations coupled to charge density oscillations and exist on the surface of metals with frequencies in the visible and infra red part of the spectrum. Localized surface plasmons are electromagnetic modes that can be exited in bounded geometries such as nanoparticles. In case of plasmon-supporting interfaces, the enhancement in transmission arises from a three-step process, the excitation of resonantly-interacting surface plasmons at the surface facing the light source, light transmission through the holes and re-emission at the other end.

In accordance with the invention, intense electromagnetic fields generated by incident radiation lead to a strong interaction of the incident fields with objects in the gap. The ability to concentrate electromagnetic energy is a property that is extremely useful and can be applied in e.g. Raman spectroscopy (in this case called surface enhanced Raman spectroscopy (SERS), the surface enhancement of the Raman scattering cross-section is proportional to the fourth power of the field enhancement factor, sensing applications, nonlinear optics, etc.

Plasmonic nano-antennas can influence the behavior of optically active molecules in several ways. Firstly, due to the focusing of electromagnetic radiation to nanovolumes, molecules can be excited more efficiently. Secondly, the plasmon resonance perturbs the local electromagnetic mode density, modifying the decay rate of local dipole emitters. In the case, e.g., of Raman spectroscopy, this double effect leads to the well known E4 dependence of the Raman scattering intensity on the local electric field.

Furthermore, in accordance with the invention, individual molecules, or even one or more segments thereof, may be detected optically. Herein, use is made of measurements of the optical transmission in combination with the application of an electric field over a specifically designed hole in the membrane. The specifically designed hole is a membrane penetrating nanostructure. a space through a membrane through which a molecule to be analyzed can pass.

A membrane penetrating nanostructure should be understood as a structure having a nanoscale passageway through which a molecule can flow. The nanostructure is preferably designed such that the degrees of freedom for the movement of the molecule in the nanostructure is limited to a predefined direction, preferably from one side of the membrane to he other side of the membrane. Preferably, the movement should be limited to a 1D movement or line movement. The pore is not limited to the region through which the molecule flows, but can be larger such that light can be coupled in the nanostructure. Therefore, the membrane penetrating nanostructure can be a nanopore, a nanoslit or a nanochannel.

Specifically, the membrane penetrating nanostructure is designed so as to create an electromagnetic hotspot. This hotspot is a location within the nanostructure at which the electromagnetic field gets concentrated. In other words, the field strength is enhanced at the hotspot due to field confinement. This field strength is the strength of an electromagnetic field resulting from the interaction of the electromagnetic radiation with the matter present. Means for enhancement of the field strength, and thus means for creation of the hotspot, include plasmon carrying metal structures, in particular nano-antennas, and a nanostructure in which cavity effects occur, particularly with a varying diameter. In the latter case, the nanostructure is preferably designed such that the hotspot is present at the position at which the—inner—diameter is smallest. However, alternative shapes of the nanostructure leading to resonance in a limited volume thereof are not excluded.

The figures of merit for this optical method according to the invention in the context of molecular analysis are spatial resolution and signal strength or signal-to-noise ratio. The plasmonic field-confinement is important in both enhancing the signals-to-be-detected and providing localization and thus spatial resolution. The plasmonic field confinement achievable is stronger than what can be achieved with traditional lens structures or photonic components. A smaller sensing region (hotspot) can thus be obtained.

The transmission-based approach provided by the present invention offers further background reduction and enhanced spatial resolution. The nanopore 6, that physically connects the upper and lower reservoir and that restricts molecular translocation and ionic current flow to a small section in the membrane, also functions as a light transmission channel in embodiments of the present invention. Hereby light transmission through the membrane via parasitic pathways, i.e. transmission through the membrane outside the pore region, is avoided. Hence, optical signals that do not interact with the optical device mounted on or in the membrane are restricted from reaching the detector, thereby eliminating unwanted background signals. A strong interaction between the light in the transmission channel and the molecule in the nanopore are thereby achieved.

This embodiment also leads to greater spatial resolution: optical signals arising from molecular excitations outside the sensing region have a reduced probability to be transmitted and to be collected by the optical detector. As a result, the embodiment provides an extra technique for achieving larger spatial resolution.

The size of the nanopore is preferably very small: critical dimension should be smaller than 100 nm and preferably smaller than 10 nm. The inner diameter of the nanopore may vary considerably depending on the intended use of the device. Typically, the channel or nanopore will have an inner diameter of at least about 0.5 nm, usually at least about 1 nm and more usually at least about 1.5 nm, where the diameter may be as great as 50 nm or longer.

Small-sized nanopores have several advantages: (1) the translocation of linear molecules can be performed with greater control in small holes: simultaneous translocation of different molecules can be avoided or the conformation of the molecule can be controlled in a better manner. (2) In some instances ionic currents through the nanopore are sensed that can provide further information about the presence of the molecule in the nanopore, or even on the structural conformation of the translocating molecule. In general, small holes give rise to a better signal-to-noise ratio for such measurement. (3) Smaller nanopore structures are expected to lead to stronger field-confinement (and thus greater spatial resolution): stronger electromagnetic fields can be excited in a plasmonic antenna when the feed-gap size is reduced. (4) The effective size of the optical transmission channel is determined by the physical size of the nanopore. Stronger background reduction can be achieved for a narrower optical channel.

It is however observed the dimensions of the nanopore may be set in dependence on the intended optical detection method and the intended molecules to be analysed. Nanopores with smallest inner diameters in the order of 1 to 5 nm are suitable for detection of at least one segment of individual molecules, for instance protein groups in DNA-strings. Nanopores with inner diameters in the range of 5 to 20 nm are suitable for detection of individual and bulky proteins. Nanopores with inner diameters in the range of 20 to 100 nm are suitable for the detection of labelled biomolecules.

In all embodiments, it is suitable that the penetrating nanostructure contains a limited volume in which resonance and field confinement occurs leading to an electromagnetic hotspot. This hotspot is then the sensing location. Transmission of electromagnetic radiation through the nanostructure will include a contribution from surface plasmon polaritons that have been excited in the hotspot.

Plasmonic materials allow guiding light in smaller volumes. The use of plasmonic properties to decrease the size of the optical transmission channel is therefore important for the present invention. Light propagation through the optical channel can occur via guided plasmonic modes or via evanescent coupling of an electromagnetic mode on the entry side to an electromagnetic mode on the exit side.

Both or either antenna structures and cavity effects can be used with the present invention. Antenna structures on the entry side help to increase the light collection efficiency and help to amplify the field intensity enhancement achievable with the channel structure itself or with the field-confining structures mounted in the channel. In accordance with a further embodiment of the present invention a gap-mode resonator is provided mounted in a surface plasmon cavity that exemplifies that antenna structures or cavities that can lead to improved performance.

The optical interaction that is exploited in the nanopore 6 can be chosen from the realm of optical spectroscopy techniques known to the skilled person. A first option is found in the amount of light transmission: the translocating molecule can modulate the transmission spectrum, information on the presence and structural information can be obtained by measuring the transmission signal. Other options are found in fluorescence, SERS, SEIRA, CARS. All these techniques greatly benefit the present invention by confinement of electromagnetic energy to a small volume to increase signal strength and spatial resolution.

For virtually all of the optical techniques listed above, signals can be enhanced by means of optical labels in accordance with an embodiment of the present invention. Fluorescence labels, SERS labels, CARS labels, quantum dots and other label-types can be chosen. Labels can be attached to the molecule under study before or during the measurement. Labels can be provided to enhance the contrast between different segments of the molecule (e.g. labels specific to nucleotides in the case of DNA sequencing) or to mark specific locations of interest on the molecule (e.g. start or end of genes in the case of DNA).

Implementations with above-described devices assembled in an array format with the aim of improving the throughput are of course also claimed.

The molecule to be investigated can be, for example a DNA molecule, RNA molecule, polysaccharide, polypeptide or protein, lipids . . . .

Nano-antennas can enhance, inter alia, the following spectroscopy methods:

I Surface enhanced Raman scattering (SERS) Enables probing vibrational transitions using optical excitation, Strongly depends on the local E-field (E4). Additional enhancement can be achieved using resonance Raman (illuminating in resonance with an electronic transition of the target molecule) or coherent anti-stokes Raman scattering (CARS) (a non-linear, 4-wave mixing process)

II Molecular fluorescence. Often used in the context of fluorescent labels, for e.g. optical microscopy applications, or microarrays. Can be enhanced or quenched by plasmonic nanostructures, depending on the geometry.

III Surface Enhanced Infrared Absorption spectroscopy, Probes directly the vibrational transitions, but has different selection rules with respect to Raman, such that it is a complimentary technique.

FIGURE DESCRIPTION

FIG. 1 presents a sketch of an apparatus in accordance with an embodiment of the present invention. (The illustration is non-limiting and not to scale, some components in the drawing are not always required.) Two fluidic reservoirs 2, 4 are separated by a membrane 5 in which a membrane penetrating nanostructure such as a nanopore 6 is fabricated. A linear molecule such as comprising nucleic acids, DNA, RNA, single-stranded, double-stranded or triple stranded and any chemical modifications thereof a strand of DNA is translocated through the solid-state nanopore 6 by means of any suitable driving force, e.g. by electrophoresis. To this end, at least one electrode 3, 5 is mounted in each reservoir 2, 4, respectively and a voltage is supplied with a voltage regulator 10 (preferably feedback coupled). The device further consists of a source of electromagnetic radiation such as a light source 8 (which can be, for example, a LED, a laser incandescent lamp or any other type of light source) and optionally a lens system 13. The light source may be placed inside the upper reservoir or may be external to the upper reservoir and may illuminate the nanopore 6 through a window. In some instances (for example CARS spectroscopy) more than one light source is used. The light is supplied from the top, i.e. from the upper reservoir 2 towards the lower reservoir 4. In the apparatus of FIG. 1 orthogonal light excitation is assumed but other angles of incidence at the nanopore 6 can also be chosen. The light interacts with the molecule inside the nanopore 6, this interaction is the basis for biomolecular analysis. Hence the nanopore can be an optical confinement. Important for the present invention is the fact that electromagnetic radiation such as light that has been transmitted through the nanopore 6 (rather than only reflected light) is used for the measurements. To this end specific optical functionality is built-in the nanopore 6. In the lower reservoir an optical detector 12 and a light capture system such as a lens system 14 are mounted that collect the transmitted light. The detector 12 may be located outside the lower reservoir and may view the nanopore 6 through a window in the lower reservoir. The output of the detector 12 may be supplied to an amplifier 7 such as a preamplifier and the out put of the amplifier may be connected to read-out electronics. The read-out electronics may include a computing unit 9.

Figure 2:
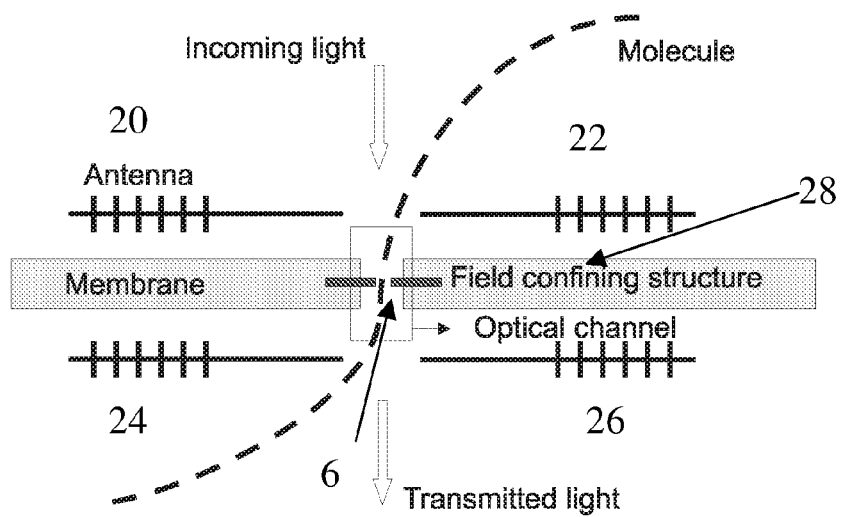
FIG. 2: schematic representation of the solid-state nanopore with electromagnetic functionality

Hence, the membrane penetrating nanostructure such as a nanopore 6 itself can be an optical device, an optical confinement with carefully designed optical properties. FIG. 2 displays a sketch of the membrane penetrating nanostructure such as a nanopore 6 that clarifies its functioning. (Again, the illustration is non-limiting and not to scale, and some components in the drawing are not always required.) A membrane penetrating nanostructure should be understood as a structure having a nanoscale passageway through which a molecule can flow. The nanostructure is preferably designed such that the degrees of freedom for the movement of the molecule in the nanostructure is limited to a predefined direction, preferably from one side of he membrane to he other side of the membrane. Preferably, the movement should be limited to a 1D movement or line movement. The pore can be round, spherical, rectangular or can have any shape and can have a varying diameter across the thickness of the membrane. The pore is not limited to the region through which the molecule flows, but can be larger such that light can be coupled in the nanostructure. Therefore, the membrane penetrating nanostructure can be a nanopore, a nanoslit or a nanochannel.

Other than as fluidic channel and passage for molecules, the membrane penetrating nanostructure such as the nanopore 6 acts as a channel for light transmission. In order to achieve light transmission through the sub-wavelength hole, the properties of surface plasmons polaritons are used. The transition of e.m. radiation through the penetrating nanostructure is a combination of up to three effects: surface plasmons, transmission of light and re-emission. Surface plasmons relates to free space e.m. radiation (the impinging radiation) being converted to surface plasmon polaritons in the coupled pore/cavity system. The dipolar excitation in the pore decays radiatively, resulting in enhanced transmission. So the transmission of e.m. radiation (or enhanced transmission) through the nanostructure is at least by excitation of surface plasmon polaritons in the nanostructure.

Furthermore, by optimizing the design of the pore/cavity system, i.e. nanostructuring the membrane on top to maximize the capture process and nanostructuring the backside to maximize the re-emission process, the transmission can be improved further and/or maximized. Transmission of light through this optical channel can occur based on two principles: via waveguiding of propagating modes in the channel or via evanescent non-propagating modes that couple through the channel to modes on the exit side {Genet2007}.

Preferably, the nanopore is narrow and further equipped with a field confining structure 28 (e.g. nanoparticle(s) or a restricting channel constriction) that create an electromagnetic hotspot. The hotspot is the location where the optical interaction is strongest and where structural or chemical information is harvested. Below will be described in some detail a particular geometry that combines all of the above features.

Antenna structures 20, 22 can be added on the light entry side to increase the portion of incident light that is collected and to achieve stronger field intensity in the nanopore 6. On the light exit side an antenna 24, 26 can be used to increase the portion of light that is converted into free-space propagating light and/or to shape the exit beam (more details supplied below).

The radiation pattern of the light exiting the membrane can be controlled through design: a dipolar radiation pattern, for example, can be achieved, or, in a more sophisticated implementation, antenna structures 24, 26 on the exit side can be provided to guide the light. This feature can be important for improving signal-to-noise and further reduction of background signals: the optical collection system in the lower reservoir can be optimized for collecting light emanating from the nano-aperture, a directed output signal can be detected with greater efficiency and leads to a better signal-to-noise. Furthermore, unwanted light collection is further suppressed. In the example of FIG. 1, this can be achieved with a lens 14 and a pinhole 16 placed in a conjugate plane.

An aspect of the present invention is that antennas 20, 22 can be employed to confine low-energy electromagnetic radiation, using their non-linear properties. For increasing degrees of field confinement, nonlinear effects become more important. These effects include wave mixing, meaning that locally electromagnetic waves with designed energies can be excited. Wave mixing includes second harmonic generation, sum frequency generation, difference frequency generation (all of these are 3-wave mixing) and four-wave mixing. Using e.g. difference frequency generation, locally low-energy electromagnetic waves can be excited. Gutjahr-Loser et al employed the non-linear properties of a scanning-electron-tunneling microscope to convert high-energy electromagnetic radiation (THz) to low-energy radiation (GHz), and succeeded in exciting local ferrimagnetic resonances in a ferrimagnetic material using THz light irradiation. Similarly, using plasmonic nano-antennas, in accordance with an aspect of the present invention magnetic resonances can be excited on a local (nano) scale. This allows local excitation of ferromagnetic resonance (FMR), electron spin resonance (ESR), and nuclear magnetic resonance (NMR). Due to its chemical selectivity, especially NMR is particularly attractive. Usually NMR is being used on macro-scale samples due to the difficulty to localize magnetic fields.

In the following fabrication schemes nanopore geometries are provided for various designs of the nanopores with optical functionality described above (see FIG. 3) in accordance with embodiments of the present invention. One embodiment will be described in detail. Rectangular and triangular hole shapes are included within the scope of the present invention. The membranes are optionally coated with metal on both sides or only on the entry or exit side. Suitable metals are gold and silver, Cu or Al. Antennas can optionally be added on one or on both sides. In embodiments described below groove patterns are illustrated. Solid-state pores in membranes can be fabricated with the numerous techniques known in the art. For example dry or wet etching can be used.

Figure 3:
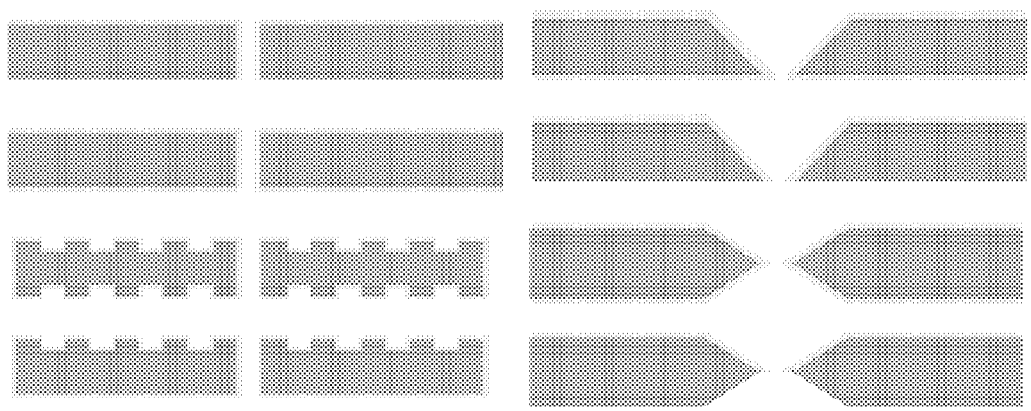
FIG. 3: various proposals for nanopore geometries.

All the geometries depicted in FIG. 3 represent cross-sections of the pore region. The term nanopore should be construed broadly to include nanoslits (two-dimensional equivalent) or nanochannels FIG. 3, left column, third row, shows in a diagrammatical, cross-sectional view a membrane with a first surface and a second surface, which first and second surface comprises plasmon-directing metal structures in the form of gratings. FIG. 3, left column, fourth row, shows in a diagrammatical, cross-sectional view a membrane with a first surface and a second surface, of which merely the first surface comprises plasmon-directing metal structures in the form of one or more grating. The second surface is herein covered with a metal layer, for instance of gold (Au). The metal layer also extends within the nanopore. The grating on the first surface results in a confinement of the electric field generated by interaction of the electromagnetic radiation with the matter, e.g. the membrane. The grating on the first surface further results in reflection of excited plasmons, so that these are returned into the nanopore, and more in particularly into the electromagnetic hotspot therein. The grating on the second surface is optional. This gratings enhances extra-ordinary transmission. Application thereof makes sense in combination with a collimated bundle of electromagnetic radiation.

FIG. 3 right column, first row, shows in a diagrammatical, cross-sectional view a membrane with a first and a second surface and a penetrating nanostructure extending in between of the first and the second surface. The penetrating nanostructure of this example is a nanopore having an inner diameter and an outer diameter. The outer diameter is located in a plane defined by the first surface. The inner diameter is defined in a plane defined by the second surface. The nanopore has a sidewall including an oblique angle with the first surface of the membrane. These sidewalls effectively constitute a field confining structure, and in particular a restricting channel restriction. The inner diameter is preferably in the range of 0.5 to 10 nm. The outer diameter is preferably in the range of 50 to 200 nm. The present structure enables confinement of the field not merely within the pore, but within the restricted volume at the inner diameter. Importantly, the effective gap suitable for translocation turns out to be even smaller than the inner diameter. An inner diameter of approximately 7 nm results in a gap suitably for translocation of molecules of approximately 2 nm. Since a nucleotide within a DNA molecule has a size of approximately 0.3 nm, this implies that at most 10 nucleotide bases will be measured simultaneously.

FIG. 3 right column, third row, shows in a diagrammatical, cross-sectional view a membrane with a first and a second surface and a penetrating nanostructure extending in between of the first and the second surface. The penetrating nanostructure of this example is a nanopore having an inner diameter and an outer diameter. In this embodiment, the inner diameter, and therewith the hotspot is located at a height between the first and the second surface of the membrane. Such a structure with more symmetry is deemed beneficial for improvement of transmission. It is observed that a perfect symmetry (e.g. that the hotspot is halfway between the first and second surface) is not needed in order to obtain an improved transmission.

As indicated in the different geometries shown in FIG. 3 as a light grey layer, the surfaces of the membrane and the nanopore are typically covered with a metal. It is most advantageous to combine a restricting channel restriction as shown in the geometries of the right column and field confining structures on at least one surface of the membrane as shown in the left column, third and fourth rows.

While the FIG. 3 show cross-sectional views, it is to be understood, that typically the nanopore extends as a slit. The restricting channel restriction may further provide a restriction in that there is merely a hole-shaped aperture in the slit, instead of a full slit. Such a structure is suitably obtained in that a dielectric layer is present at the height of the hotspot, e.g. near to the second surface of the membrane. This dielectric layer is suitably optically transparent for the electromagnetic radiation in use. A hole is defined in this dielectric layer. Such a hole is for instance made by electron beam irradiation.

EXAMPLE

Figure 4:
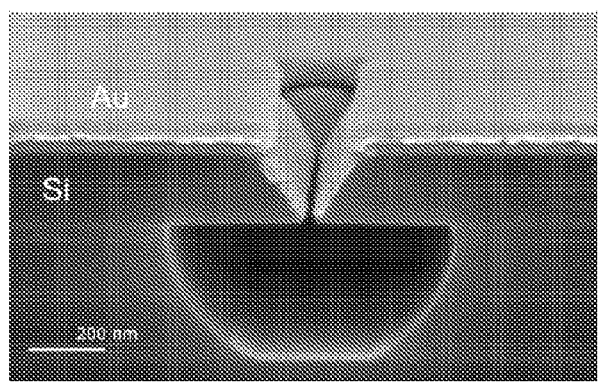
FIG. 4: Scanning electron micrograph of a KOH etched slit, the structure was cleaved in order to reveal its cross-section. The structure was coated with Au and acts as a resonant optical antenna.

An embodiment of the present invention will be described with reference to a controllable SERS substrate and a cavity formed using KOH with feed gap. In this embodiment use is made of anisotropic etching of silicon in KOH or TMAH etch solutions to create a nanopore. In such etch solution, the chemical etching of silicon along the <111> crystal direction is greatly retarded with respect to etching along the <100> crystal direction. Building on this property, pyramidal etch-pits or triangular slits can be defined enclosed by (111) crystal planes. (100) SOI material (Silicon on Insulator) can be used as the substrate. FIG. 4 shows a scanning electron micrograph of the obtained structure. Note that the slit is, in this case, not made in a membrane, membranes can be obtained through etching of the silicon backside material. The structure was coated with Au and acts as a resonant optical antenna and a considerable portion of the light impinging on the structures is transmitted. Greatest field confinement is achieved in the gap and the gap mode is responsible for the greatest share of light transmission.

The KOH pit acts as a resonant cavity for surface plasmon on the metal sidewalls of the pits. The resonance condition of the etch-pit depends on the size of the cavity and the wavelength of the surface plasmon polariton. In the geometry of this embodiment having a KOH-etched groove with a slit at the bottom, these cavity effects are equally important. Use was made of a Finite Difference Time Domain (FDTD) solver to investigate the optical properties of this pit-with-slit-geometry. A two-dimensional model was made that can accurately render the behavior of long slits as pyramidal etch-pits behave similarly but 3D models are needed to render the behavior of such slit geometry accurately. The thickness of the silicon top layer was taken to be 750 nm, a Au layer with a uniform thickness of 60 nm covers the silicon structure.

Figure 5:
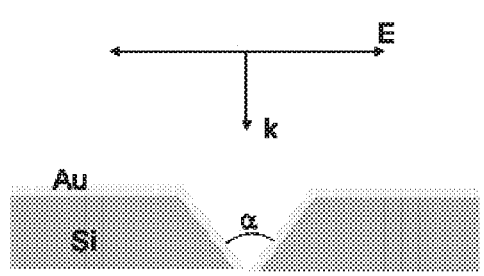
FIG. 5: (a) Sketch of the two-dimensional model (angle=68 degrees, defined by silicon crystal structure and KOH etch properties. (log $|E_x|^2$)<ode profiles at different frequencies of excitation (b) THz (c) THs (d) THz. A standing wave pattern is developed.
Figure 5:
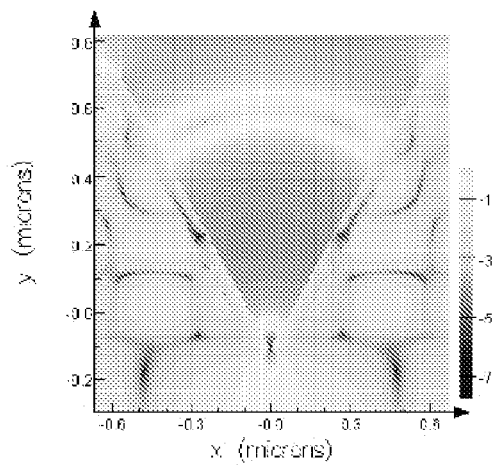
Figure 5:
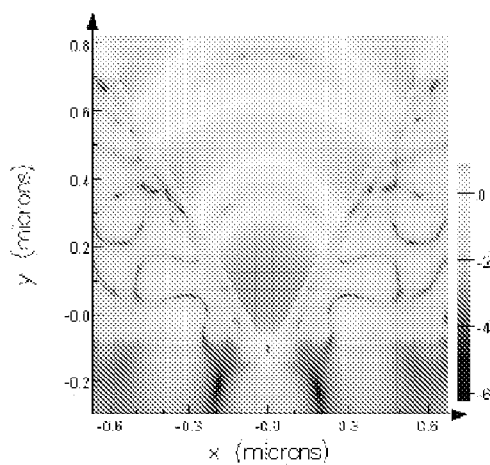
Figure 5:
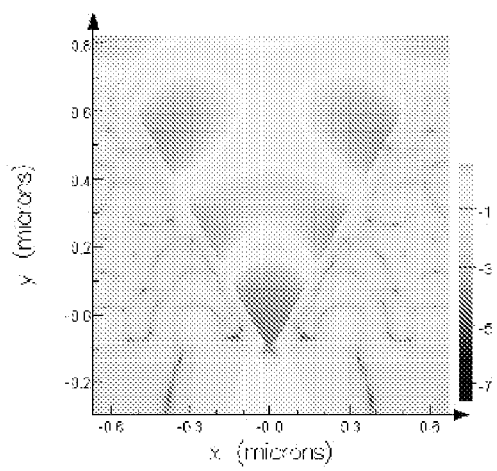
Figure 6:
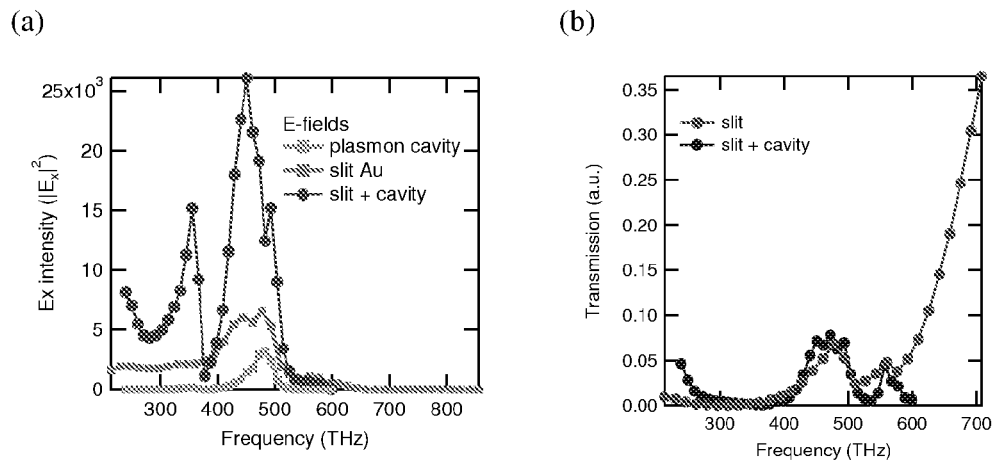
FIG. 6: (a) Field intensity spectra ($|E_x|^2$). (b) Transmission spectra
FIG. 7: a plot of transmission efficiency for point dipole source as function of position in the geometry.

In FIG. 5 (a) the model is illustrated schematically. In panels (b), (c) and (d) of the same figure mode profiles at different frequencies of excitation are represented ($\log|Ex|2$). A clear standing wave pattern is developed, evidence for constructive interference in the cavity. The narrow slit at the bottom of the groove strongly influences the optical properties of the overall structure. In a second model, the optical properties of thin triangular slits in accordance with another embodiment were investigated in order to study the effect of the slit separately. In this model use was made of a 50 nm thick gold film with triangular holes etched in them. Field intensity in the center of the slit is plotted in FIG. 6. The structure has a clear resonance at 480 THz. In the same plot the field intensity versus frequency graph is provided for an etch groove without slit, a 2-dimensional variant of the geometry investigated in reference {Perney2006, Perney2007}. In this case the field intensity was probed at the apex of the triangular groove. In the same figure the field intensity probed in a groove-with-slit geometry is plotted. It is clear that this third spectrum contains features from the pure slit-mode and the cavity mode of the groove. The cavity amplifies the slit mode and functions as an antenna. The field intensity in the gap and at resonance is expected to depend on the antenna arm length: one expects an enhanced field intensity when the antenna is matched to the gap resonance. In literature, such feedgap coupled to an antenna is occasionally termed resonant optical antenna.

In panel (b) of the same FIG. 5 the transmission spectra for a gold membrane with triangular pit and the slit mounted in a cavity are plotted. The transmission efficiency on resonance is substantial (10% of plane wave radiation is transmitted). Note that the high efficiency of transmission at frequencies >600 THz for the triangular slit is due to the transparency of gold in this frequency regime, the triangular slit does not have a great influence on the total transmission in this part of the spectrum.

The above results provide insight in the functioning of the KOH-defined slits as resonant optical antenna with strong enhancement of the attainable field-confinement and local field intensity, and also elucidates that a significant portion of the impinging light can be transmitted through a narrow portion of such geometry. 3D simulations on KOH defined etch pits with a square hole at the bottom (opposed to long rectangular slits in KOH-etched grooves) reveal that in terms of field-intensity slits are the better choice. This is due to a better charge separation, or, put alternatively, elimination of charge-shunting currents for the slit geometry.

In the embodiment described above, the cavity is defined by the sidewalls of the etch-pit. Other types of cavities or antenna structures can also be considered. Metal antenna structures consisting of corrugations in a metal film such as in some of the examples drawings of FIG. 3. Additionally, photonic cavities (made with dielectric materials) can also be coupled to the plasmonic antenna-mode resonator in the channel {Kim1999}.

Figure 7:
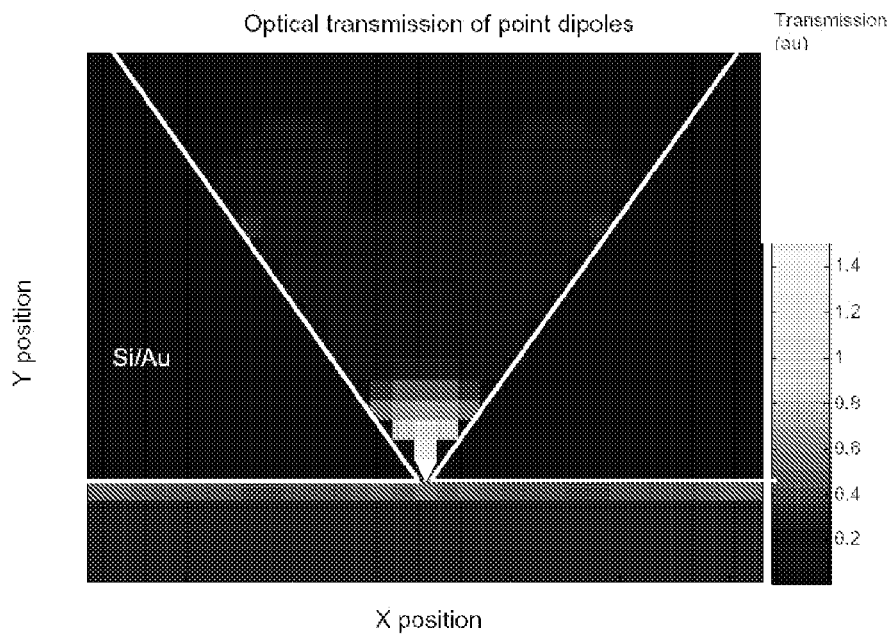

The above described geometry in combination with a transmission based measurement can lead to enhanced spatial resolution. The transmission efficiency of light generated by point dipoles placed at different locations in the geometry (dipole orientation: along the x-axis) have been calculated. The result of all calculations is summarized in the plot of FIG. 7. This 'transmission matrix' indicates that a dipole excited close to the feedgap has a much greater transmission efficiency than a dipole placed at a larger distance from the hotspot. Unwanted signals, arising from molecules or part of a molecule outside the sensing area, therefore contribute less to the total collected signal.

It is observed for clarity that the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

REFERENCES

C. Dekker, 'Solid-state nanopores', Nature nanotech., 2, 209-215 (2007).

D. W. Deamer, M. Akeson, 'Nanopores and nucleic acids: prospects for ultrarapid sequencing.' Trends Biotechnol. 18, 131-180 (2000).

F. J. Garcia de Abajo, 'Colloquium: Light scattering by particle and hole arrays', Rev. Mod. Phys. 79, 1267 (2007).

D. E. Grupp, H. J. Lezec, T. Thio, T. W. Ebbesen, 'Beyond the Bethe Limit: Tunable Enhanced Light Transmission Through a Single Sub-Wavelength Aperture', Adv. Mater. 11, 860 (1999).

H. J. Lezec, A. Degiron, E. Devaux, R. A. Linke, L. Martin-Moreno, F. J. Garcia-Vidal and T. W. Ebbesen, 'Beaming Light from a Subwavelength Aperture', Science 297, 820 (2002).

E. Prodan, C. Radloff, N. J. Halas and P. Nordlander, 'A Hybridization Model for the Plasmon Response of Complex Nanostructures', Science 302, 419 (2003).

P. J. Schuck, D. P. Fromm, A. Sundaramurthy, G. S. Kino and W. E. Moerner, 'Improving the Mismatch between Light and Nanoscale Objects with Gold Bowtie Nanoantennas', Phys. Rev. Lett. 94, 017402 (2005).

C. Genet and T. W. Ebbesen, 'Light in tiny holes', Nature, 445, 39 (2007).

R. M. M. Smeets, U. F. Keyser, N. H. Dekker and C. Dekker, 'Noise in solid-state nanorpores' PNAS 105, 417 (2008).

P. Muhlschlegel, H.-J. Eisel, O. J. F. Martin, B. Hecht, D. W. Pohl, 'Resonant optical antennas' Science, 308, 1607 (2005).

N. M. B. Perney, F. J. Garcia Abajo, J. J. Baumberg, A. Tang, C. M. Netti, M. D. B. Charlton and M. E. Zoorob, 'Tuning localized plasmon cavities for optimized surface-enhanced Raman scattering', Phys. Rev. B 76, 035426 (2007).

N. M. B. Perney, J. J. Baumberg, M. E. Zoorob, M. D. B. Charlton, S. Mahnkopf and C. M. Netti, 'Tuning localized plasmons in nanostructured substrates for surface-enhanced Raman scattering' Opt. Express 14, 847 (2006).

W. Kim, V. P. Safono, V. M. Shalaev and R. L. Armstrong, Fractals in microcavities: Giant coupled, multiplicative enhancement of optical responses, Phys. Rev. Lett. 82, 4811 (1999).

The invention claimed is:

1. An apparatus comprising:
a membrane having a first and a second major surface and having a membrane-penetrating nanostructure between the first and second major surfaces, the membrane-penetrating nanostructure having an inner surface, the membrane being coated with metal on its first major surface and its second major surface and on the inner surface of the membrane-penetrating nanostructure, the metal coated on the inner surface of the membrane-penetrating nanostructure being continuous with the metal coated on the first major surface and the metal coated on the second major surface,
a source of electromagnetic radiation that impinges radiation on the membrane-penetrating nanostructure in the direction of the first major surface,
means for translocating molecules through the membrane-penetrating nanostructure, and
a detection unit for detecting electromagnetic radiation that exits from the membrane-penetrating nanostructure away from the second major surface, transmission of electromagnetic radiation through the membrane-penetrating nanostructure being at least by excitation of surface plasmon polaritons in the membrane-penetrating nanostructure,
wherein the membrane-penetrating nanostructure is further equipped with a field confining structure that creates an electromagnetic hotspot.

2. The apparatus according to claim 1, further comprising a first and second chamber, wherein the membrane is disposed between the first chamber and the second chamber.

3. The apparatus of claim 1, wherein the means for translocating includes electrodes disposed on either side of the membrane and connected to a source of electrical power.

4. The apparatus of claim 2, wherein the source of electromagnetic radiation is disposed in or adjacent the first chamber, the apparatus further comprising an optical detector disposed in the second chamber or disposed next to the second chamber.

5. The apparatus of claim 1, wherein the field confining structure comprises one or more nanoparticles or a restricting channel constriction.

6. The apparatus of claim 5, wherein the membrane-penetrating nanostructure comprises a nanopore with an inner diameter and an outer diameter, said restricting channel constriction defining the inner diameter and said outer diameter being defined at the first surface of the membrane, a side wall of the nanopore extending between said first surface and said restricting channel constriction including an oblique angle with reference to the first surface.

7. The apparatus of claim 1 further comprising at least one antenna structure on the first major surface of the membrane adapted to increase a portion of incident radiation that is collected and to achieve stronger field intensity in the membrane-penetrating nanostructure.

8. The apparatus according to claim 1 further comprising at least one an antenna located on the second major surface adapted to increase a portion of radiation that is converted into free-space propagating radiation, to shape an exit radiation beam, or both.

9. The apparatus according to claim 1, wherein the membrane-penetrating nanostructure is a pore or hole, a slit or a channel.

10. The apparatus according to claim 9, wherein the membrane-penetrating nanostructure is a nanopore, having a size with a critical dimension smaller than 100 nm.

11. The apparatus according to claim 1 wherein the electromagnetic radiation has a wavelength and the membrane-penetrating nanostructure has a size that is sub-wavelength.

12. The apparatus according to claim 1, wherein the first major surface has an antenna structure formed therein, the antenna structure being coated by the metal coating.

13. The apparatus according to claim 12, wherein the antenna structure is a surface grating.

14. The apparatus according to claim 1, wherein the second major surface has an antenna structure formed therein, the antenna structure being coated by the metal coating.

15. The apparatus according to claim 14, wherein the antenna structure is a surface grating.

16. The apparatus according to claim 1, wherein the metal is gold or copper.

17. The apparatus according to claim 1, wherein the membrane is formed from silicon.

18. A method for use with a membrane having a first and a second major surface and having a membrane-penetrating nanostructure between the first and second major surfaces, the membrane-penetrating nanostructure having an inner surface, which membrane-penetrating nanostructure is equipped with a field confining structure, the membrane being coated with metal on its first major surface and its second major surface and on the inner surface of the membrane-penetrating nanostructure, the metal coated on the inner surface of the membrane-penetrating nanostructure being continuous with the metal coated on the first major surface and the metal coated on the second major surface, the method comprising:
    directing electromagnetic radiation onto the nanostructure in the direction of the first major surface, so as to create an electromagnetic hotspot in the membrane-penetrating nanostructure,
    translocating molecules through the membrane-penetrating nanostructure,
    detecting electromagnetic radiation that exists from the nanostructure away from the second major surface, transmission of electromagnetic radiation through the membrane-penetrating nanostructure being at least by excitation of surface plasmon polaritons in the membrane-penetrating nanostructure.

19. The method as claimed in claim 18, wherein the detection of electromagnetic radiation occurs by molecular spectroscopy.

20. The method as claimed in claim 19, wherein Raman spectroscopy is used.

21. The method according to claim 18, wherein the first major surface has a first antenna structure formed therein and the second major surface has a second antenna structure formed therein, the first antenna structure and the second antenna structure being coated by the metal coating.

22. The apparatus according to claim 21, wherein the antenna structure is a surface grating.

23. The apparatus according to claim 18, wherein the metal is gold or copper.

* * * * *